US011234776B2

(12) United States Patent
McGrogan et al.

(10) Patent No.: US 11,234,776 B2
(45) Date of Patent: Feb. 1, 2022

(54) ROTATING ASSISTANT PORT

(71) Applicant: Intuitive Surgical Operations, Inc., Sunnyvale, CA (US)

(72) Inventors: Anthony K McGrogan, San Jose, CA (US); Craig R. Ramstad, Minden, NV (US); Paul E. Lilagan, Sunnyvale, CA (US); Michael Ikeda, Saratoga, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 174 days.

(21) Appl. No.: 16/661,918

(22) Filed: Oct. 23, 2019

(65) Prior Publication Data

US 2020/0054404 A1 Feb. 20, 2020

Related U.S. Application Data

(63) Continuation of application No. 14/211,433, filed on Mar. 14, 2014, now Pat. No. 10,470,827.
(Continued)

(51) Int. Cl.
*A61B 1/32* (2006.01)
*A61B 34/30* (2016.01)
(Continued)

(52) U.S. Cl.
CPC .......... *A61B 34/30* (2016.02); *A61B 17/3421* (2013.01); *A61B 17/3423* (2013.01); *A61B 17/0281* (2013.01); *A61B 2017/347* (2013.01); *A61B 2017/3445* (2013.01); *A61B 2017/3466* (2013.01)

(58) Field of Classification Search
CPC . A61B 17/34; A61B 17/3417–17/3462; A61B 1/32; A61M 39/02
See application file for complete search history.

(56) References Cited

U.S. PATENT DOCUMENTS 5,906,577 A * 5/1999 Beane ................ A61B 17/3431
600/207
5,954,687 A * 9/1999 Baudino ............... A61M 39/02
604/48

(Continued)

FOREIGN PATENT DOCUMENTS

CN 101822553 A 9/2010
DE 202012102878 U1 8/2012
(Continued)

OTHER PUBLICATIONS

Extended European Search Report for Application No. 14765610.2, dated Aug. 25, 2016, 10 pages.
(Continued)

*Primary Examiner* — Eduardo C Robert
*Assistant Examiner* — Steven J Cotroneo
(74) *Attorney, Agent, or Firm* — Schwegman Lundberg & Woessner, P.A.

(57) ABSTRACT

Embodiments of a rotating assistant port device are presented. The assistant port device can be utilized to provide for additional assistant instruments in single port robotic surgery. In some embodiments, the assistant port device can be utilized for skin retraction during single port teleoperated robotic surgery.

18 Claims, 6 Drawing Sheets

Related U.S. Application Data

(60) Provisional application No. 61/792,218, filed on Mar. 15, 2013.

(51) Int. Cl.
*A61B 17/34* (2006.01)
*A61B 17/02* (2006.01)

(56) References Cited

U.S. PATENT DOCUMENTS

| | | | |
|---|---|---|---|
| 5,984,921 A * | 11/1999 | Long | A61B 17/34 606/48 |
| 6,068,593 A * | 5/2000 | Krauter | A61B 1/042 600/135 |
| 6,077,288 A * | 6/2000 | Shimomura | A61B 17/3423 604/167.01 |
| 6,123,689 A | 9/2000 | To et al. | |
| 6,254,534 B1 | 7/2001 | Butler et al. | |
| 6,578,577 B2 | 6/2003 | Bonadio et al. | |
| 6,582,364 B2 | 6/2003 | Butler et al. | |
| 6,623,426 B2 | 9/2003 | Bonadio et al. | |
| 6,846,287 B2 | 1/2005 | Bonadio et al. | |
| 6,869,393 B2 | 3/2005 | Butler | |
| 7,081,089 B2 | 7/2006 | Bonadio et al. | |
| 7,195,590 B2 | 3/2007 | Butler et al. | |
| 7,300,399 B2 | 11/2007 | Bonadio et al. | |
| 7,445,597 B2 | 11/2008 | Butler et al. | |
| 8,092,430 B2 | 1/2012 | Richard et al. | |
| 8,206,294 B2 * | 6/2012 | Widenhouse | A61B 17/3462 600/210 |
| 8,376,938 B2 | 2/2013 | Morgan et al. | |
| 10,470,827 B2 | 11/2019 | McGrogan et al. | |
| 2006/0020241 A1 | 1/2006 | Piskun et al. | |
| 2009/0221966 A1 * | 9/2009 | Richard | A61B 17/3423 604/164.04 |
| 2010/0081395 A1 | 4/2010 | Widenhouse et al. | |
| 2010/0081882 A1 * | 4/2010 | Hess | A61B 17/3423 600/203 |
| 2010/0081995 A1 * | 4/2010 | Widenhouse | A61B 17/3462 604/164.08 |
| 2010/0228198 A1 | 9/2010 | Widenhouse et al. | |
| 2010/0249694 A1 | 9/2010 | Choi et al. | |
| 2010/0312063 A1 | 12/2010 | Hess et al. | |
| 2011/0124967 A1 * | 5/2011 | Morgan | A61B 17/3423 600/204 |
| 2011/0201883 A1 * | 8/2011 | Cooper | A61B 1/00064 600/109 |
| 2011/0277775 A1 * | 11/2011 | Holop | A61B 17/3423 128/849 |
| 2011/0295077 A1 | 12/2011 | Stefanchik et al. | |
| 2012/0078058 A1 | 3/2012 | Richard et al. | |

FOREIGN PATENT DOCUMENTS

| | | |
|---|---|---|
| EP | 2226026 A1 | 9/2010 |
| EP | 2374420 A2 | 10/2011 |
| JP | 2009101150 A | 5/2009 |
| JP | 2009207888 A | 9/2009 |
| JP | 2019082452 A | 4/2010 |
| JP | 2010099460 A | 5/2010 |
| JP | 2010207577 A | 9/2010 |
| JP | 2010207579 A | 9/2010 |
| JP | 2010221021 A | 10/2010 |
| JP | 2013503022 A | 1/2013 |
| WO | WO-2010128738 A1 | 11/2010 |
| WO | WO-2012044959 A1 | 4/2012 |

OTHER PUBLICATIONS

International Search Report and Written Opinion for application No. PCT/US14/28550, dated Jul. 18, 2014, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ROTATING ASSISTANT PORT

RELATED APPLICATIONS

This application is a continuation of and claims the benefit of priority under 35 U.S.C. § 120 to U.S. patent application Ser. No. 14/211,433, filed on Mar. 14, 2014, which claims priority to U.S. Provisional Application Ser. No. 61/792,218 filed on Mar. 15, 2013, each of which is herein incorporated by reference in its entirety.

TECHNICAL FIELD

Embodiments of the present invention are related to robotic surgery and, in particular, to a rotating assistant port that can be used with robotic surgery.

DISCUSSION OF RELATED ART

Minimally invasive surgery (MIS) (e.g., endoscopy, laparoscopy, thoracoscopy, cystoscopy, and the like) allows a patient to be operated upon through small incisions by using a camera and elongated surgical instruments introduced to an internal surgical site. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

One or more cannulas may be passed through small (generally 1 inch or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments externally to the surgical site under the view provided by the camera instrument.

It is typical to provide several cannulas for a minimally invasive surgical procedure. Such a system is the da Vinci system sold by Intuitive Surgical. Generally each cannula will provide access to the surgical site for a single surgical or camera instrument. For example, four cannulas may be provided with one cannula being used to introduce a camera instrument and the remaining three cannulas being used to introduce surgical instruments. While the small incisions necessary for placing a cannula are less traumatic than the incision necessary for open surgery, each incision still represents a trauma to the patient.

In an effort to reduce the trauma of minimally invasive surgery even further, techniques are being developed to allow minimally invasive surgery using only a single cannula. This may be accomplished by using a somewhat larger cannula that can accommodate all of the instruments required for the surgery. Minimally invasive surgery performed through a single cannula may be referred to as single port access (SPA) surgery. The single cannula may be introduced through a body orifice or through an incision.

If multiple surgical instruments and/or camera instruments are to be introduced to a surgical site through a single cannula, it can become difficult to manage the instruments within the cannula. It is desirable to use as small a cannula as possible consistent with the size of the instruments to be passed through the cannula. This may make it difficult to introduce the additional instruments and to maintain the necessary mobility of the instruments.

In either case, the instruments that are passed through the cannula may be robotically controlled. However, in such cases it is more difficult to provide further instruments that are hand controlled to assist with the robotically controlled surgery.

Therefore, there is a need to develop systems for better access to the surgical area.

SUMMARY

In accordance with aspects of the present invention, a rotating assistant port device includes a circular elastomeric element; a sleeve coupled to the circular elastomeric element; a sleeve mount coupled to the sleeve opposite the circular elastomeric element; an outer hub removably attached to the sleeve mount; and an inner hub captured between the sleeve mount and the outer hub, the inner hub including a cannula port. In some embodiments, the inner hub further includes at least one assisting cannula port.

A rotatable assistant port kit according to some embodiments can include one or more wound protectors, each wound protector including a circular elastomeric element, a sleeve coupled to the circular elastomeric element, and a sleeve mount coupled to the sleeve opposite the circular elastomeric element; an outer hub attachable to the sleeve mount of one of the wound protectors; and an inner hub that is capturable between the outer hub and the sleeve mount, wherein the one or more wound protectors allow for variation of a body wall thickness.

A method of robotic single-port surgery according to some embodiments of the present invention includes forming an incision in a body wall of a body; inserting a wound protector that includes a circular elastomeric element, a sleeve coupled to the circular elastomeric element, and a sleeve mount coupled to the sleeve opposite the circular elastomeric element, the wound protector being inserted such that the circular elastomeric element is inside the body and the sleeve mount is outside the body; placing a cannula through a cannula port of an inner hub; placing the inner hub such that the cannula is inserted through the incision and the inner hub is positioned against the sleeve mount; installing an outer hub to hold the inner hub positioned against the sleeve mount; docking a teleoperated robot to the cannula; and inserting teleoperated instruments through the cannula.

These and other embodiments are further discussed below with respect to the following figures.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Further, this description's terminology is not intended to limit the scope of the invention. For example, spatially relative terms such as "beneath", "below", "lower", "above", "upper", "proximal", "distal", "horizontal", "vertical" and the like may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Figure 1:
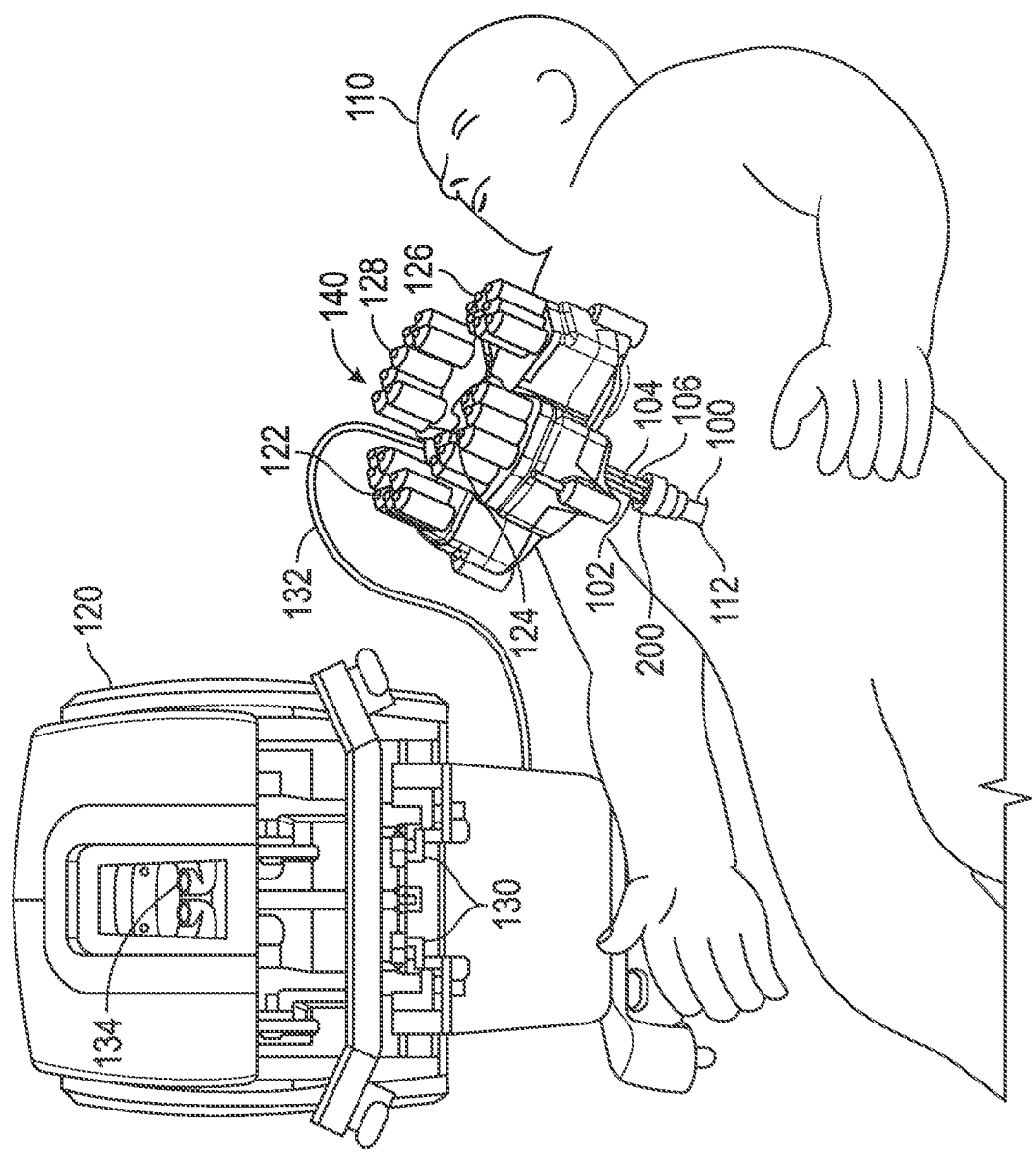
FIG. 1 illustrates a single-port teleoperated robotic surgical system.

FIG. 1 shows a pictorial view of a minimally invasive surgery on a patient 110 using single port access for robotic surgical instruments 102, 104, 106. Single port access involves a cannula 100 inserted through a single incision 112. Typically three or four surgical instruments, including a camera instrument, are introduced through cannula 100. In addition, there will generally be provisions for introducing an insufflation gas, such as carbon dioxide ($CO_2$), at or near cannula 100. It will be appreciated that single port surgery utilizes a substantial amount of equipment located in a small amount of space.

The teleoperated robotic surgical instruments 102, 104, and 106, which may include a camera instrument that may provide images of the surgical site and other instruments, are coupled to actuators 122, 124, 126, and 128. Actuators 122, 124, 126, and 128 are servo actuators that allow a surgeon to manipulate the surgical instruments using a computer mediated control station 120 and are mounted on teleoperated robot 140. These manipulations may include functions such as positioning, grasping, and moving. Such actuator control of surgical instruments may be referred to as teleorobotic surgery. Actuators 122, 124, 126, and 128 of teleoperated robot 140 may be supported on a separate structural arm that, once positioned, can be fixed relative to patient 110.

A control system couples a computer mediated control station 120 to the robotic actuators 122, 124, 126, and 128. The control system may coordinate movement of the input devices with the movement of their associated surgical instruments so that the images of the surgical instruments 102, 104, 106, as displayed to the surgeon, appear at least substantially connected to the input devices in the hands of the surgeon. Further levels of connection will also often be provided to enhance the surgeon's dexterity and ease of use of the surgical instruments 102, 104, and 106.

The computer mediated control station 120 may provide hand operated controllers 130 that allow manipulation of the teleorobotic surgical instruments 102, 104, 106 by transmitting signals, such as electrical control signals provided by cables 132, to the actuators 122, 124, 126, and 128 that control the actions of the coupled surgical instruments 102, 104, and 106. Typically one of the surgical instruments 102 will be a camera instrument that is manipulated to place the remaining surgical instruments and the objects being manipulated within a field of view of the camera. The camera instrument transmits signals to the control station 120 so that an image captured by the camera of the instruments and objects within the field of view can be displayed on a visual display 134 that is viewed by the surgeon as the coupled surgical instruments 104, 106 are manipulated. The hand operated controllers 128 and the visual display 130 may be arranged to provide an intuitive control of the surgical instruments 104, 106, wherein the instruments respond in an expected manner to movements of the controllers.

Figure 2:
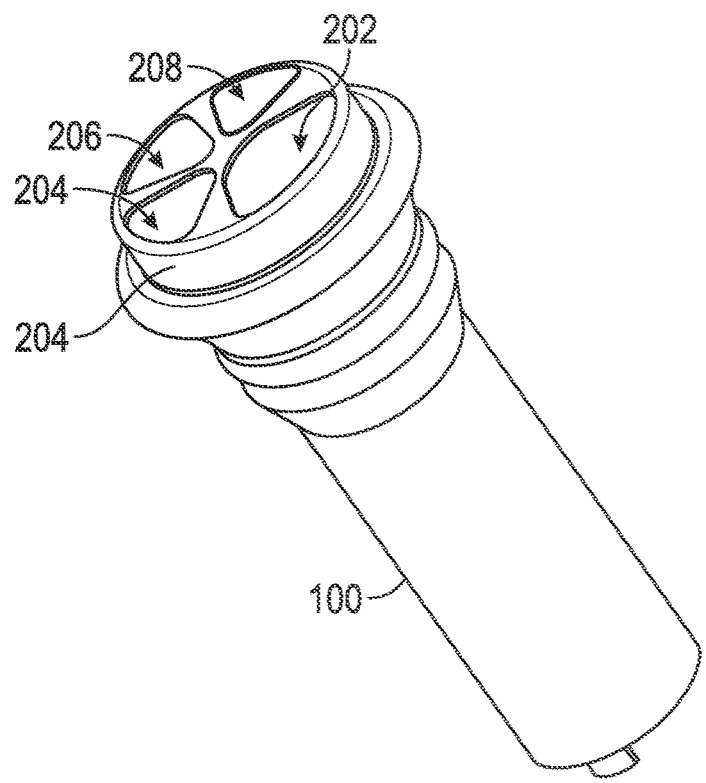
FIG. 2 illustrates a single-port cannula.
Figure 3:
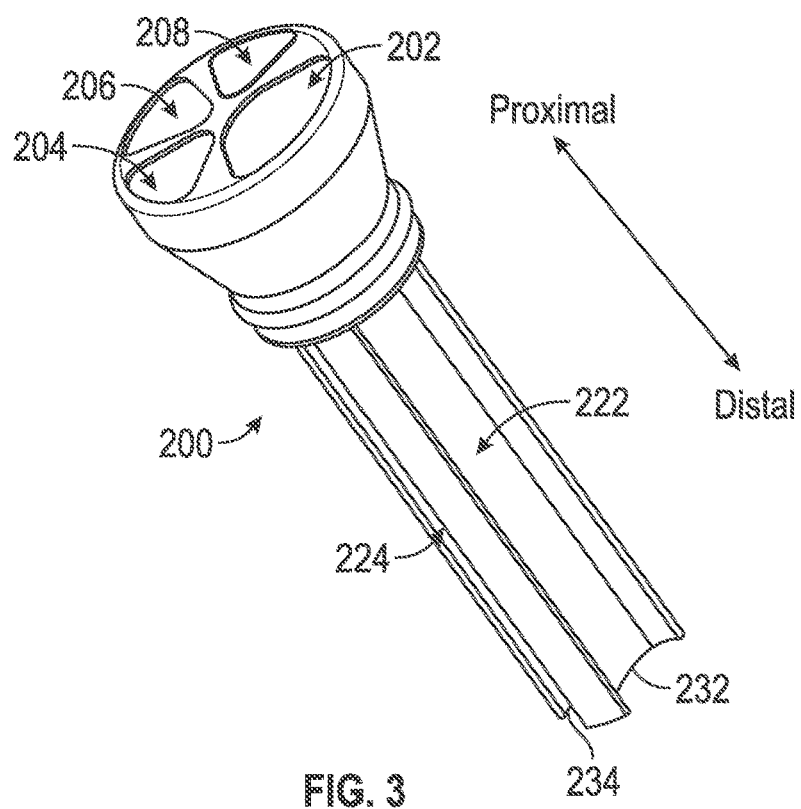
FIG. 3 illustrates a guide insert of the single-port cannula illustrated in FIG. 2.

FIG. 2 shows a pictorial view of an access port that provides the single port access shown in FIG. 1. The access port includes a cannula 100, which includes an instrument guide 200 that is inserted into the cannula to guide multiple instruments through cannula 100 to facilitate single port access. FIG. 3 is a pictorial view of instrument guide 200. Instrument guide 200 is configured to fit closely within cannula 100. Instrument guide 200 includes a number of guide channels 222, 224. Each of the guide channels 222, 224 is configured to support a single surgical instrument 102, 104, 106 at a defined position within the cannula 100. Surgical instruments 102, 104, 106 are inserted into the access port through openings 202, 204, 206, 208 at a proximal end of the instrument guide 200. Surgical instruments 102, 104, 106 are supported by the guide channels 222, 224 until they emerge from a distal end 232, 234 of the instrument guide 200. The instrument guide may be formed from an electrically non-conductive material to aid in electrically isolating the instruments which may carry an electrical charge used for cauterization.

In spite of the availability of several teleorobotically controlled instruments 102, 104, and 106 that can be extended through guide channels 222 and 224 in cannula 100, in some procedures it may be advantageous to provide for further instruments to be utilized at the surgical site, to provide for retraction at incision 112, or to provide for both further instruments and retraction. In some applications, a second incision can be provided adjacent to incision 112 and a second, hand-held, instrument can be inserted through the second incision. Such second instruments can include, for example, needles, suction, retraction, or other instruments. The problem, however, is that often the second incision will tear because of the torque on the tissue between the two incisions, resulting in a loss of insufflation.

Figure 4A:
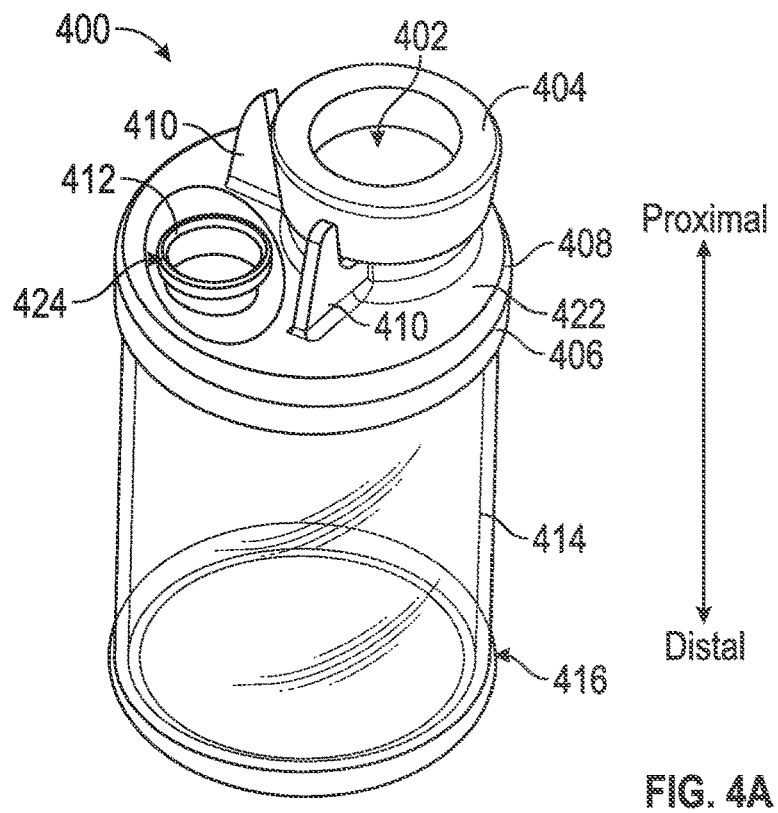
FIGS. 4A and 4B illustrate a rotating assistant port device that can be utilized with the single-port cannula illustrated in FIG. 2.
Figure 4B:
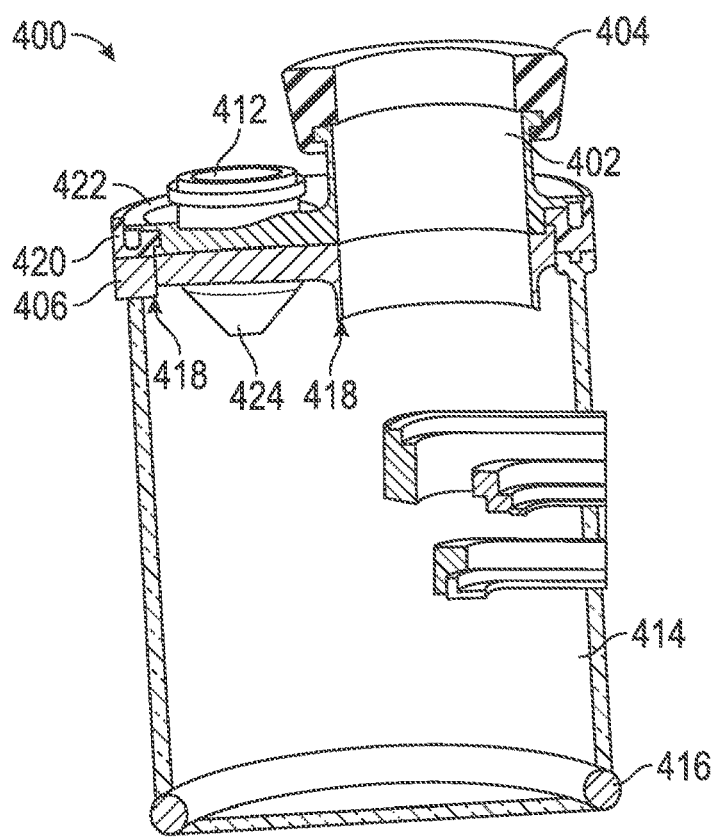

FIGS. 4A and 4B illustrate a rotatable assistant port device 400 according to some embodiments of the present invention that can be utilized to provide access for second hand-operated instruments. FIG. 4A shows an isometric view of assistant port device 400 and FIG. 4B illustrates a section view of assistant port 400. As shown in FIGS. 4A and 4B, rotatable assistant port device 400 includes a cannula port 402 and an assisting port 412. Cannula port 402 accommodates insertion of cannula 100, which in some embodiments can be a single-port cannula that is coupled to a teleoperated robot 140 as described above. Assisting port 412 accommodates insertion of a single instrument cannula for utilization with a hand-operated instrument or a single instrument itself. A single-port cannula inserted into cannula port 402 can be fixed by teleoperated robot 140. Assisting port 412 can then be rotated around cannula port 402, providing for a wide range of access to the surgical area.

As illustrated in FIGS. 4A and 4B, the distal portion of rotatable assistant port device 400 includes a circular elastomeric element 416 connected to a thin plastic material that forms a body wall protective sleeve 414 and a supporting ring or sleeve mount 406. Together, circular elastomeric element 416, protective sleeve 414, and supporting ring 406 form a tube, which can be referred to as a wound protector.

Figure 5:
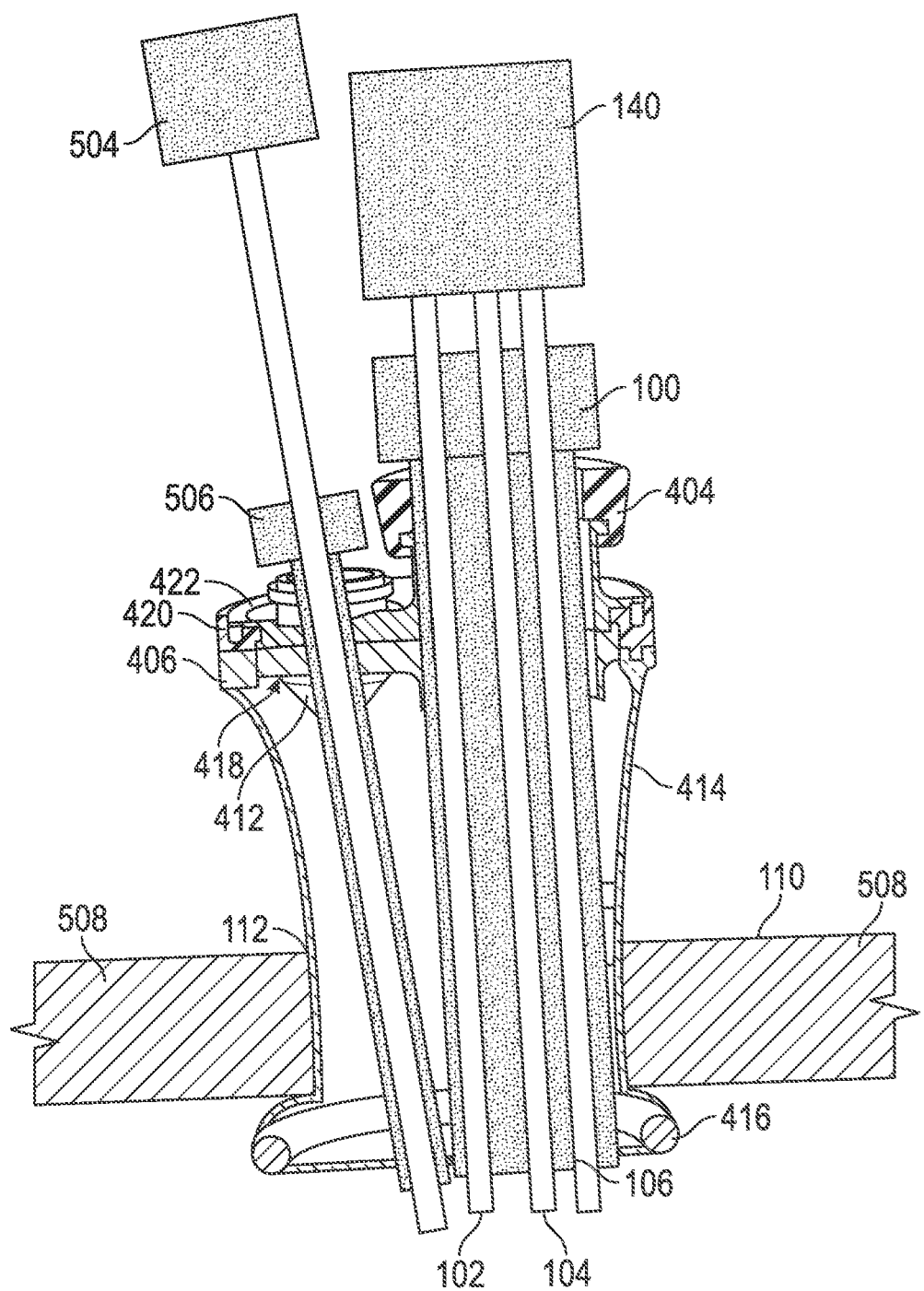
FIG. 5 illustrates utilization of the rotating assistant port device illustrated in FIGS. 4A and 4B.

FIG. 5 illustrates that, during surgery, incision 112, which is large enough to accommodate both cannula 100 and cannula 506, is placed in the skin and underlying tissue, the body wall 508. The circular elastomeric element 416 is slid through the skin incision to the underside of the body wall 508. When in place, the elastomeric component 416 expands and forms an anchor on the underside of body wall 508. Sleeve portion 414 lands on the incised skin area and forms, in part, the wound protector. Sleeve mount 406 is outside of the body on the surface of the skin. As such, sleeve portion 414 may be sufficiently long to accommodate any thickness of body wall 508.

As is further shown in FIGS. 4A and 4B, an outer hub 420 can be attached to sleeve mount 406, in some embodiments snapping into sleeve mount 406. A release mechanism 408 can hold outer hub 420 fixed with respect to sleeve mount 406. An inner hub assembly 422 can be captured between sleeve mount 406 and outer hub 420 such that inner hub assembly 422 can be rotated with respect to sleeve mount 406. After completion of a procedure, inner hub assembly 422 can be removed by releasing outer hub 420 with release mechanism 408, leaving the wound protector, sleeve mount 406, sleeve 414, and circular elastomeric element 416, fixed.

Outer hub 420 can be attached to sleeve mount 406 in any fashion that captures inner hub 422 in rotatable fashion between outer hub assembly 420 and sleeve mount 406. Latching mechanism 408 can, for example, by a friction clamp. Alternatively, sleeve mount 406 may be threaded and outer hub 420 may be screwed onto sleeve mount 406. In some embodiments, a "pickle jar" arrangement can be made where outer hub 420 screws, for example a turn and a half, onto threads formed in sleeve mount 406 such that inner hub 422 is captured between outer hub 420 and sleeve mount 406. A seal 418 can be provided between inner hub 422 and sleeve mount 406 such that inner hub 422 rotates with respect to sleeve mount 406 while insufflation pressure is maintained.

As shown in FIGS. 4A and 4B, inner hub assembly 422 can rotate relative to outer hub 420. Inner hub assembly 422 includes assisting cannula port 412 and cannula port 402. As discussed above, cannula 100, which can be inserted through cannula port 402, can be fixedly attached to teleoperated robot 140. Cannula clamp 404 is rotatably attached to cannula port 402. As such, as illustrated in FIG. 5, cannula clamp 404 attaches inner hub assembly 422 to cannula 100 inserted through cannula port 402. Cannula clamp 404 can be any type of locking clamp and may provide a locking mechanism to fix inner hub assembly 422, and therefore all of rotatable assistant port device 400, to cannula 100. Cannula clamp 404 can enable robot 140 to utilize device 400 in retracting body wall 508.

As such, cannula clamp 404 and the interface between inner hub 422 and outer hub 420 provide for two rotary joints. Between these rotary joints, inner hub 422 can be rotated around a fixed cannula 100 positioned through cannula port 402, and therefore can be rotated relative to patient 110. To assist in rotating inner hub 422, finger grips 410 formed in inner hub 422 can be provided. As a result, cannula 506 can be rotated around cannula 100 by rotating inner hub 422. During the process circular elastomeric element 416, sleeve 414, and sleeve mount 406 remain substantially fixed. Sleeve 414 may position to accommodate the orientation of inner hub 422 with respect to the fixed cannula 100.

Assistant port device 400 also maintains surgical insufflation gas. As discussed above, insufflation gas is introduced through cannula 100 to inflate surgical area 508. As shown in FIGS. 4A and 4B, rotary lip seal 418 between outer hub 420 and sleeve mount 406 and between inner hub 422 and cannula 100 in cannula port 402. Additionally, assisting cannula port 412 includes a seal 424 to seal on assisting instruments as they are introduced to the surgical site.

In some embodiments, rotary lip seal 418 can be separated into an o-ring type seal that seals between inner hub 422 and sleeve mount 406 and an o-ring type seal around cannula port 402. As shown in FIG. 4A, assistant cannula port 412 can includes an insert seal 424 that seals around assisting cannula 506 or, in cases where assisting cannula 506 is not utilized, seals around surgical instrument 504. In some embodiments, rotary lip seal 418 can be formed of a single piece that includes all of the sealing functions, including the function of insert seal 424 and rotary lip seal 418. In some embodiments, insert seal 424 can be similar to seals described in U.S. Pat. No. 6,123,689, which is herein incorporated by reference in its entirety.

As illustrated in FIG. 5, rotating assistant port device 400 enables single port robotic surgery. In other words, all surgical tasks can be accomplished through a single skin incision 112. Teleoperated surgical robot 140 operates instruments 102, 104, and 106 through cannula 100 that is inserted through cannula port 402. In some embodiments, assistant activity can occur with a surgical instrument inserted through cannula port 402 with a limited range of motion, function, and utility. However, assistant activity can occur through assistant port 412. As shown in FIG. 5, an assistant cannula 506 can be inserted through assistant port 412 and a hand operated instrument 504 inserted through cannula 506.

In some embodiments, hand operated instrument 504 can be inserted through assistant cannula port 412 without a cannula 506. In some embodiments, assistant port 412 can include a guide, such as a ball, through which instrument 504 can be inserted. The ball may act as a ball-joint for guidance of instrument 504 into incision 112.

As discussed above, seals 418 and seals in assistant port 412, along with cannula seals in cannulas 506 and 100, maintain insufflation pressure. Insufflation pressure can be maintained through a wide range of instruments, for example instrument 504 can be 5-13 mm instruments. Further, instrument 504 can be removed or exchanged throughout the surgical procedure as needed.

Inner hub 422 is attached and supported by cannula 100, which allows the assistant port 412 to act as a fulcrum point for performing procedures with instrument 504. Because the fulcrum point formed by assistant port 412 also swivels around cannula 100, and therefore around the surgical site, assistant port 412 provides a large range of motion to the operator and a large anatomical access area. Finger grips 410 allow the user to easily twist inner hub 422 around cannula 100 for good operation. The rotary nature of device 400 allows assisting surgical instrument 504 to rest alongside cannula 100 as it works. This arrangement allows incision 112 to be relatively small, only slightly larger than needed to accommodate both cannula 100 and cannula 506.

The presence of device 400 also allows cannula 100 to be inserted to a shallow depth and still function. The shallow or short cannula allows teleorobotic instruments 102, 104, and 106 to deploy and operate as early as possible and close to body wall 508. Therefore, anatomy located near to body wall 508 can be more effectively accessed by teleoperated robot 140 without risk of loosing the port site (i.e., cannula 100 popping out of body wall 508 and subsequent loss of insufflation gas).

In some embodiments, device 400 can be supplied as a kit that includes inner hub 422, multiple seal inserts 424 for assisting cannula port 412 that accommodates various sizes of instruments 504 or cannulas 506, seal 418, outer hub 420, and multiple wound protectors (sleeve mount 406, sleeve 414, and circular elastomeric element 416). Multiple wound protectors can be placed in the kit, each wound protector varying by length of sleeve 414 to accommodate different thicknesses of body wall 508 and may also vary by stiffness of circular elastomeric element 416 to accommodate different retraction pressures from robot 140. In some embodiments, sleeve 414 may be adjustable in length. In some embodiments, as discussed above, seal 418 and seal insert 424 can be formed in a single piece, in which case the kit may include multiple versions of the single piece seals to accommodate different cannulas 506 or, if cannula 506 is not used, different instruments 504.

Figure 6A:
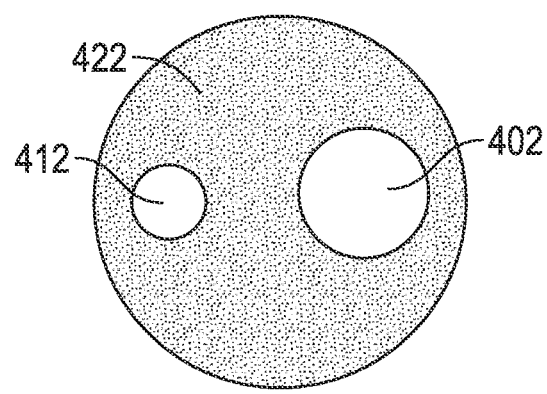
FIGS. 6A, 6B, 6C, 6D, and 6E illustrate example of arrangements of ports in a rotating assistant port device.
Figure 6B:
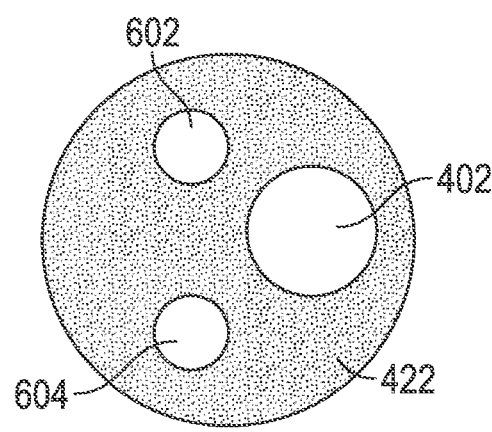
Figure 6C:
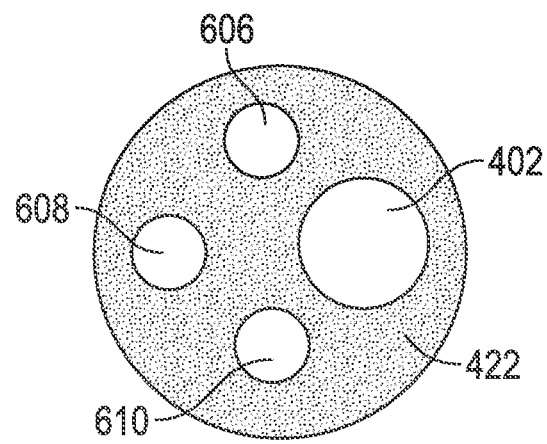
Figure 6D:
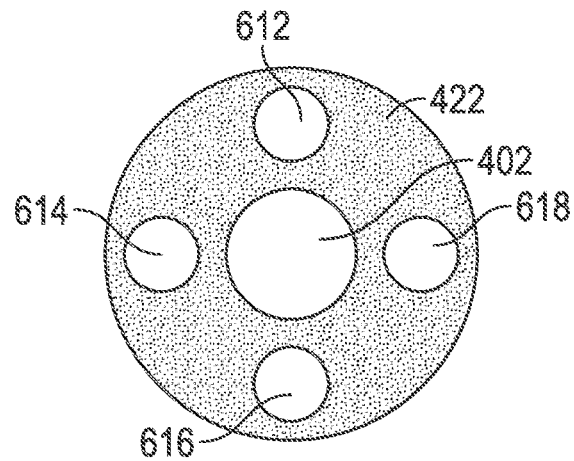
Figure 6E:
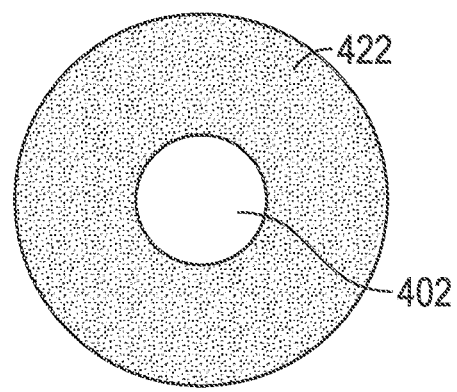

Device 400 is shown with a single assistant port 412. However, embodiments of the present invention can include any number of assistant ports 412 or no assistant port 412. Some example arrangements of ports are illustrated in FIGS. 6A, 6B, 6C, 6D, and 6E. FIG. 6A illustrates the arrangement of ports illustrated in FIGS. 4A and 4B. As shown in FIG. 6A, a single assistant port 412 is positioned near an off-center cannula port 402 on inner hub 422. FIG. 6B illustrates an arrangement with two assistant ports 602 and 604 positioned near an off-center cannula port 402. In some examples, assistant ports 602 and 604 may be positioned at 90° from each other, FIG. 6C illustrates three assistant ports 606, 608, and 610 positioned near an off-center cannula port 402. As shown in FIG. 6D, in some embodiments cannula port 402 can be positioned towards the center of inner hub 422 and two or more assistant ports, ports 612, 614, 616, and 618 are illustrated, positions around cannula port 402. FIG. 6E illustrates an embodiment that does not include an assistant port 412. Additional assistant ports allows for insertion of multiple instruments 506, but may increase the size of device 400 and the resulting incision 112 that is needed.

Figure 7A:
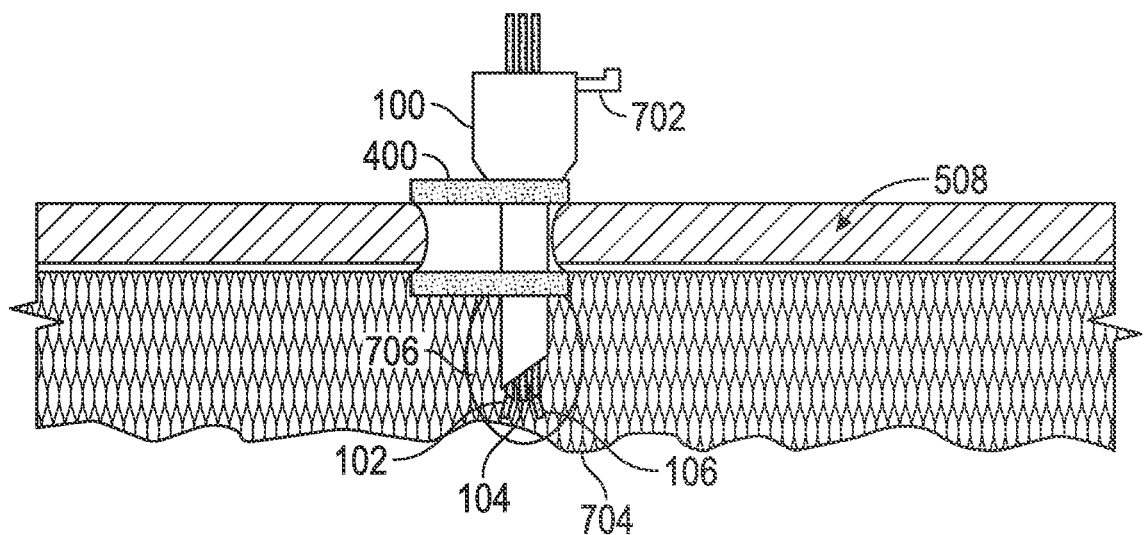
FIGS. 7A and 7B illustrate further utilization of the rotating assistant port device.
Figure 7B:
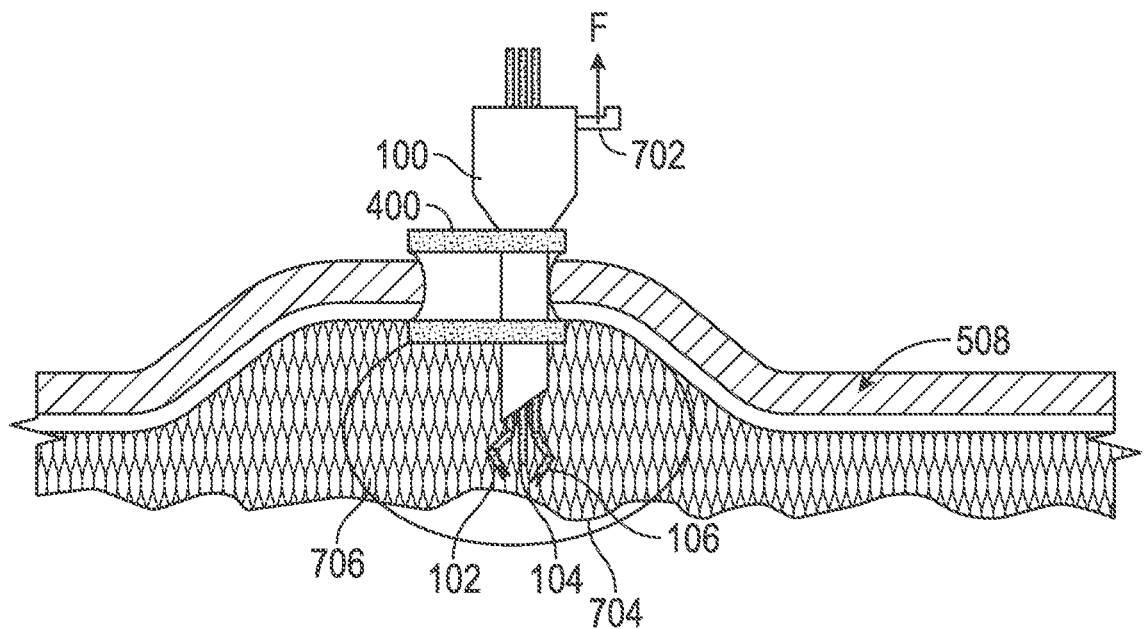

FIGS. 7A and 7B illustrate utilizing device 400 for retracting body wall 508. FIG. 7A illustrates device 400 clamped to cannula 100. As shown in FIG. 7A, cannula 100 includes an attachment 702 that attaches cannula 100 to teleoperated robot 140. As shown in FIG. 7A instruments 102, 104, and 106 have an effective working area 706 in which to work on the target structure 704.

FIG. 7B illustrates retraction of body wall 508 by applying a force F on cannula 100. As discussed above, device 400 can be locked to cannula 100 with cannula clamp 404. Additionally, cannula 100 is locked to teleoperated robot 140 with robot attachment 702, which provides a rigidly fixed position for cannula 100, and therefore for cannula port 402, with respect to teleoperated robot 140. When device 400 is installed and locked onto cannula 100, teleoperated robot 140 can subsequently be lifted upward, retracting body wall 508. The retraction force is supported by cannula 100 through device 400, where circular elastomeric element 416 pulls body wall 508 in the direction of the applied force and helps provide space for surgical instruments to operate and perform surgery. In the case of loss of insufflation, retraction of device 400 can also be utilized to place tension on body wall 508. As shown in FIG. 7B, the effective working area 706 in order to access structure 704 can be substantially larger with the retraction. For example, body wall 508 can be retracted by as much as a couple of centimeters utilizing teleoperated robot 140.

As illustrated in FIG. 7B, because device 400 has elastomeric element 416, which is inserted inside body wall 508, and is clamped with cannula clamp 404 to cannula 100, which is attached to teleoperated robot 140, the surgeon can move teleoperated robot 140 such that wall 508 is pulled in an advantageous direction to expose planes and anatomy at target structure 704. Teleoperated robot 140 can be repositioned as required by hospital staff. As show in FIG. 7B, device 400 can be utilized as a skin retractor and provides additional space for performing a procedure.

Similar retraction can be accomplished by a cannula 100 inserted into the body and positioned so that the cannula tube and wall 508 are close to parallel. Cannula 100 can then be pulled to lift wall 508, however there is a concern over additional trauma that may result. Further, target structure 704 may not be advantageously exposed to instruments through cannula 100. Additionally, cannula 100 may pop out of wall 508 in the process. Utilizing device 400, port loss is not a concern and advantageously exposing the desired target structure 704 is easily accomplished. Additionally, during the retraction process cannula 100 may be pulled further away from target structure 704, allowing instruments 102, 104, and 106 to fully deploy into the much larger working area 706. This allows better utilization of all instruments and also allows a camera to be more advantageously positioned for focus, field of view, and visual purchase relative to target structure 704. Further, instruments 102, 104, and 106 can triangulate into the surgical site of target structure 704, providing the surgeon a more intuitive working position.

In some embodiments, for example as shown in FIG. 6E, device 400 may not utilize an assistant port 412 at all. FIG. 6E shows an example device 400 with a centered cannula port 402 and no assistant ports 412. Device 400, with retraction, may provide sufficient access to target structure 704 to perform the surgical procedure without the need for additional instruments.

As shown in FIGS. 4A and 4B, inner hub 422 can be rotated such that assistant port 412 can be positioned at any location around cannula port 402. Further, assistant port 412 can be repositioned multiple times during a surgical procedure. Further, multiple instruments 504 can be utilized through assistant port 412 during a surgical procedure. In practice, however, teleoperated robot 140 and the shape of cannula 100, including insufflation pressure hoses and ports, etc., limit the full range of motion of assistant port 412 around cannula port 402. In some embodiments, the range of motion of assistant port 412 around cannula port 402 can be as much as 300°.

Device 400 can be formed from polycarbonate, silicon, and polyurethane. In particular, inner hub 422, outer hub 420, and sleeve mount 406 can be formed of polycarbonate.

Sleeve 414 can be formed of polyurethane. Seals, for example seal inserts 424 and seal 418, can be formed of silicon seals.

In a surgical operation, an incision 112 can be formed in the body wall and the wound protector inserted through the incision 112 such that circular elastomeric element 416 is positioned against the bottom of body wall 508 while sleeve mount 406 is positioned on the top of body wall 508. Cannula 100 can then be positioned into cannula port 402 of inner hub 422 and insert seal 424 positioned into assistant cannula port 412. Cannula 100 can then be positioned through incision 112 and inner hub 422 positioned against sleeve mount 406. Cannula 100 can then be clamped to inner hub 422 with cannula clamp 404. Outer hub can then be installed to hold inner hub in place and finish assembly of device 400. Teleoperated robot 140 can then be docked to cannula 100 and instruments 102, 104, and 106 inserted through cannula 100. During the surgical procedure, teleoperated robot 140 controls instruments 102, 104, and 106 while an assistant utilizes surgical instruments 506 through assistant port 412. Further, additional retraction can be placed on body wall 508 as needed by teleoperated robot 140 applying an upward force on device 400 through clamp 404 and inner hub 422.

The above detailed description is provided to illustrate specific embodiments of the present invention and is not intended to be limiting. Numerous variations and modifications within the scope of the present invention are possible. The present invention is set forth in the following claims.

What is claimed is:

1. A surgical system comprising:
a cannula configured to be fixed-in-space relative to a patient by being coupled to a structural arm of a teleoperated robot;
a body wall protective sleeve;
a sleeve mount coupled to the body wall protective sleeve;
an outer hub removably attached to the sleeve mount; and
an inner hub captured between the sleeve mount and the outer hub, the inner hub including a cannula port and an assistant port, the inner hub being rotatable relative to the outer hub and around the cannula inserted through the cannula port, the assistant port being configured to accommodate insertion of a hand operated instrument, the hand operated instrument and the assistant port being rotatable together around the cannula and the cannula port as the inner hub rotates around the cannula and the cannula port while an orientation of the outer hub and the sleeve mount remains substantially fixed.

2. The surgical system of claim 1, wherein the assistant port is configured to accommodate insertion of an assistant cannula, the hand operated instrument being inserted through the assistant cannula.

3. The surgical system of claim 2, further including a seal insert in the assistant port.

4. The surgical system of claim 1, further including a seal between the inner hub and the sleeve mount.

5. The surgical system of claim 1, further including a seal in the cannula port.

6. The surgical system of claim 1, further including finger grips in the inner hub to use for rotation of the at least one assistant port around the cannula and the cannula port.

7. The surgical system of claim 1, further including a cannula clamp rotatably attached to the inner hub at the cannula port, the cannula clamp clamping around the cannula inserted into the cannula port.

8. The surgical system of claim 1, wherein the outer hub is attached to the sleeve mount with a release mechanism.

9. The surgical system of claim 1, wherein the outer hub engages threads formed in the sleeve mount.

10. The surgical system of claim 1, further comprising a seal between the inner hub and the sleeve mount, the seal being configured to enable the inner huh to rotate with respect to the sleeve mount while an insufflation pressure is maintained in the sleeve.

11. The surgical system of claim 1, further comprising a circular elastomeric element, and wherein the body wall protective sleeve is coupled to the circular elastomeric element.

12. A rotatable assistant port kit, comprising:
a first wound protector and a second wound protector each including a body wall protective sleeve and a sleeve mount coupled to the sleeve, the sleeve of the first wound protector being for a first body wall thickness, and the sleeve of the second wound protector being for a second body wall thickness different from the first body wall thickness;
a first cannula and a second cannula, each of the first cannula and the second cannula being configured to be fixed-in-space relative to a patient by being coupled to a structural arm, the first cannula being for the first body wall thickness, and the second cannula being for the second body wall thickness;
an outer hub attachable to the sleeve mount of one of the first and second wound protectors; and
an inner hub between the outer hub and the sleeve mount, the inner hub including a cannula port and one or more assistant ports;
wherein the inner hub is rotatable relative to the outer hub and around either the first cannula or the second cannula inserted through the cannula port, and as a result the one or more assistant ports rotate around the either the first cannula or the second cannula as the inner hub rotates around the either the first cannula or the second cannula while an orientation of the outer hub and the sleeve mount remains substantially fixed.

13. The kit of claim 12, further comprising:
a rotary lip seal; and
one or more seal inserts, the one or more seal inserts allowing for sealing around the either the first cannula or the second cannula inserted through the cannula port.

14. The kit of claim 13, further comprising a first seal that accommodates instruments of a first size and a second seal that accommodates instruments of a second size different from the first size.

15. A surgical system comprising:
a structural arm fixed-its-space relative to a patient;
a cannula coupled to the structural arm; and
a rotating assistant port device, the rotating assistant port device comprising:
a body wall protective sleeve;
a sleeve mount coupled to the body wall protective sleeve;
an outer hub removably attached to the sleeve mount; and
an inner hub captured between the sleeve mount and the outer hub, the inner hub including a cannula port and an assistant port, the inner hub being rotatable relative to the outer hub and around the cannula inserted through the cannula port, the assistant port being configured to accommodate insertion of a hand operated instrument, the hand operated instrument and the assistant port being rotatable together around the cannula and the cannula port as the inner hub rotates around the cannula and the cannula port while an orientation of the outer hub and the sleeve mount remain substantially fixed.

16. The system of claim 15, further including finger grips in the inner hub to use for rotation of the at least one assistant port around the cannula port.

17. The system of claim 15, further including a cannula clamp rotatably attached to the inner hub at the cannula port, the cannula clamp clamping around the cannula inserted into the cannula port.

18. The system of claim 15, wherein the outer hub is attached to the sleeve mount with a release mechanism.

* * * * *

UNITED STATES PATENT AND TRADEMARK OFFICE
CERTIFICATE OF CORRECTION

PATENT NO.         : 11,234,776 B2
APPLICATION NO.    : 16/661918
DATED              : February 1, 2022
INVENTOR(S)        : McGrogan et al.

Page 1 of 1

It is certified that error appears in the above-identified patent and that said Letters Patent is hereby corrected as shown below:

In the Claims

In Column 10, Line 5, in Claim 10, delete "huh" and insert --hub-- therefor

In Column 10, Line 50, in Claim 15, delete "fixed-its-space" and insert --fixed-in-space-- therefor Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*